(12) United States Patent
Chi et al.

(10) Patent No.: US 11,285,143 B2
(45) Date of Patent: Mar. 29, 2022

(54) USE OF MTOR INHIBITOR AND CHLOROQUINE FOR TREATING CANCER

(71) Applicant: Johnpro Biotech Inc., Taipei (TW)

(72) Inventors: Kwan-Hwa Chi, Taipei (TW); Yu-Shan Wang, Taipei (TW); Yi-Chun Huang, Taipei (TW); Hsin-Chien Chiang, Taipei (TW)

(73) Assignee: Johnpro Biotech Inc., Taipei (TW)

( * ) Notice: Subject to any disclaimer, the term of this patent is extended or adjusted under 35 U.S.C. 154(b) by 260 days.

(21) Appl. No.: 16/490,892

(22) PCT Filed: Mar. 8, 2017

(86) PCT No.: PCT/CN2017/075987
§ 371 (c)(1),
(2) Date: Sep. 4, 2019

(87) PCT Pub. No.: WO2018/161279
PCT Pub. Date: Sep. 13, 2018

(65) Prior Publication Data
US 2020/0009127 A1    Jan. 9, 2020

(51) Int. Cl.
| | |
|---|---|
| A61K 31/47 | (2006.01) |
| A61P 35/00 | (2006.01) |
| A61K 31/436 | (2006.01) |
| A61K 31/573 | (2006.01) |
| A61K 38/22 | (2006.01) |
| A61K 39/395 | (2006.01) |

(52) U.S. Cl.
CPC ............ *A61K 31/47* (2013.01); *A61K 31/436* (2013.01); *A61K 31/573* (2013.01); *A61K 38/22* (2013.01); *A61K 39/3955* (2013.01); *A61P 35/00* (2018.01)

(58) Field of Classification Search
CPC .... A61K 31/47; A61K 31/436; A61K 31/573; A61K 38/22; A61K 39/3955; A61K 45/06; A61K 31/4706; A61P 35/00; C07K 16/2818
See application file for complete search history.

(56) References Cited

FOREIGN PATENT DOCUMENTS

| WO | WO-2016161615 A1 * | 10/2016 | ........... A61K 31/436 |
| WO | WO-2017019896 A1 * | 2/2017 | ......... C07K 16/2818 |

OTHER PUBLICATIONS

Graff, et al., Oncotarget, vol. 7, No. 33, Published Jul. 12, 2016 (Year: 2016).*
Sharma, et al., Cell 168, Feb. 9, 2017 (Year: 2017).*
Zhang, et al., Scientific Reports; 6 Article No. 29774 (2016) (Year: 2016).*
Dai, et al., "Abstract 59: Dual mTOR kinase inhibitor reverses rapamycin resistance in prostate cancer cells" AACR-NCI-EORTC International Conference: Molecular Targets and Cancer Therapeutics; Nov. 5-9, 2015; Boston, MA (Year: 2015).*
Ferrari, et al., Urol Int 1996;56 (suppl1) :13-17 (Year: 1996).*

\* cited by examiner

*Primary Examiner* — Julie Wu
*Assistant Examiner* — John L Van Druff

(57) ABSTRACT

Disclosed herein are uses of a mammalian target of rapamycin (mTOR) inhibitor and chloroquine or analogue thereof in the manufacture of a medicament for treating cancer patients who are not responsive to a hormone therapy and an immunotherapy. In particular, the medicament is used during the hormone therapy and the immunotherapy to sensitize the patients to the hormone therapy and the immunotherapy.

8 Claims, 2 Drawing Sheets

USE OF MTOR INHIBITOR AND CHLOROQUINE FOR TREATING CANCER

CROSS-REFERENCE TO RELATED APPLICATION

This application is a U.S. National Stage Filing under 35 U.S.C. 371 from International Patent Application Serial No. PCT/CN2017/075987, entitled "USE OF MTOR INHIBITOR AND CHLOROQUINE FOR TREATING CANCER," filed Mar. 8, 2017, and published on Sep. 13, 2018, the disclosure of which are incorporated by reference herein in their entireties.

BACKGROUND OF THE INVENTION

1. Field of the Invention

The present disclosure relates to the use of mammalian target of rapamycin (mTOR) inhibitor and chloroquine or analogues thereof to treat cancer; more particularly, to treat cancer patients who do not responsive well to a hormone therapy and immunotherapy.

2. Description of Related Art

Cancer is a class of diseases characterized by abnormal growth. There are over 100 different types of cancer, each requiring unique diagnosis and treatment. Lung, prostate, colorectal, stomach, and liver cancer are the most common types of cancer in men, while breast, colorectal, lung, uterine cervix, and stomach cancer are the most common among women. According to the most recent data from World Health Organization (WHO), there were 14 million new cancer cases and 8.2 million cancer-related deaths in 2012 worldwide.

When patients are diagnosed with cancer, the physicians will recommend a treatment plan that is most likely to have the greatest benefits and the fewest risks or side effects. This initial treatment is referred to as the first-line treatment or first-line therapy. First line therapies for cancers are usually one or a combination of, radiation therapy (radiotherapy), surgery, chemotherapy, targeted therapy, hormone therapy, and immunotherapy. However, for some patients, the first line therapy may not have worked or may have had some limited efficacy; alternatively or additionally, the first line therapy may have produced unacceptable side effects or even jeopardized the patient's life. Sometimes first line therapies show progress for a period of time followed by a stalling or continued growth of the cancer. In these cases, the second line therapy may be given. Nonetheless, there are cases where even the second line therapy is not effective, and subsequent treatments are required.

In view of the foregoing, there exists a need in the related art for improved therapies that effectively treat cancers, particularly those cancers that are not effectively treated by the first or second line therapy.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to the use of a mammalian target of rapamycin (mTOR) inhibitor and chloroquine or analogue thereof in the manufacture of a medicament for treating a cancer patient who is unresponsive to a hormone therapy and immunotherapy.

According to one embodiment of the present disclosure, the medicament comprising the mTOR inhibitor and chloroquine or analogue thereof is administered to the cancer patient during the hormone therapy and immunotherapy to sensitize the cancer patient to the hormone therapy and immunotherapy.

In certain embodiments, the medicament improves the cancer patient's NK cell cytotoxicity. For example, in some cases, after one course of treatment (e.g., 3 weeks), the NK cell cytotoxicity of the cancer patient is increased by at least 50, 60, 70, 80, 90, 100%.

Illustrative embodiments of the mTOR inhibitor include sirolimus, temsirolimus, everolimus, deforolimus, and ATP-competitive mTOR kinase inhibitors.

Non-limiting examples of chloroquine or analogue thereof is chloroquine or hydroxychloroquine.

According to certain embodiments of the present disclosure, the hormone therapy comprises leuprolide and/or cyproterone acetate.

In optional embodiments, the immunotherapy comprises an anti-PD-1 agent, such as nivolumab, pembrolizumab, or pidilizumab.

According to various embodiments of the present disclosure, the cancer patient is diagnosed with melanoma, esophageal carcinoma, gastric carcinoma, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, or head and neck squamous cell carcinoma.

In another aspect, the present disclosure is directed to a method for treating a cancer patient who is unresponsive to a hormone therapy and an immunotherapy.

According to some embodiments of the present disclosure, the method comprises the step of administering to the subject an effective amount of the hormone therapy, an effective amount of the immunotherapy, an effective amount of mTOR inhibitor, and an effective amount of chloroquine or an analogue thereof.

In still another aspect, the present disclosure is directed to a pharmaceutical composition or kit for treating a cancer patient who is unresponsive to a hormone therapy and an immunotherapy.

According to some embodiments, the pharmaceutical composition or kit comprises an effective amount of mTOR inhibitor, and an effective amount of chloroquine or an analogue thereof.

Subject matters that are also included in other aspects of the present disclosure include the use of an mTOR inhibitor and chloroquine or an analogue thereof in the manufacture of a medicament for treating a cancer patient who is unresponsive to a hormone therapy and immunotherapy, as well as an mTOR inhibitor and chloroquine or an analogue thereof.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1:
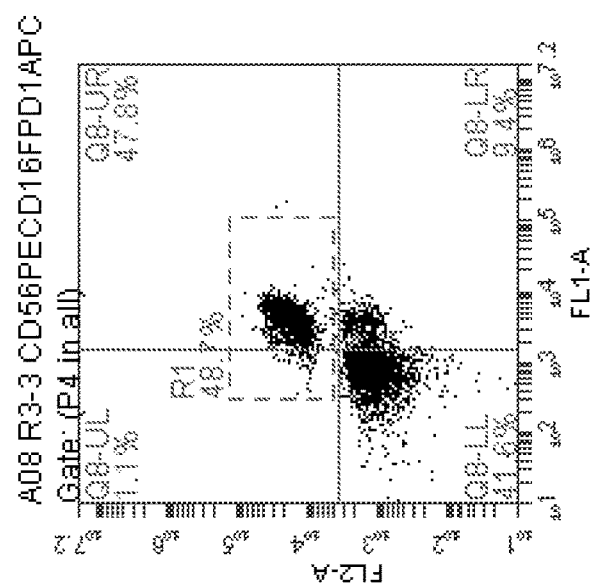
FIG. 1 and FIG. 2 are dot plots of the flow cytometry analysis according to one working example of the present disclosure.
Figure 1:
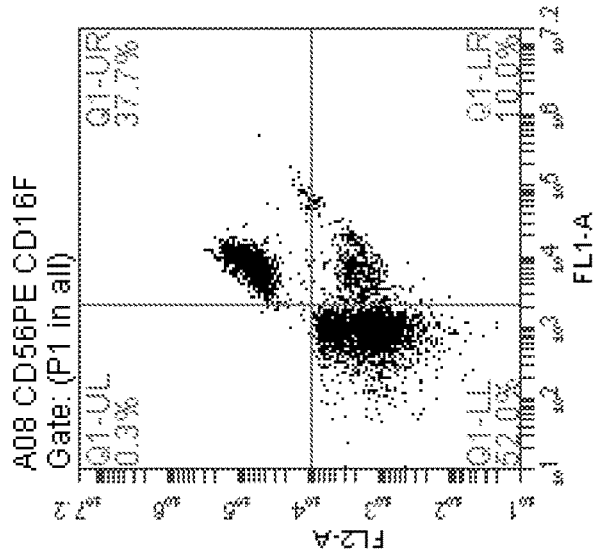
Figure 1:
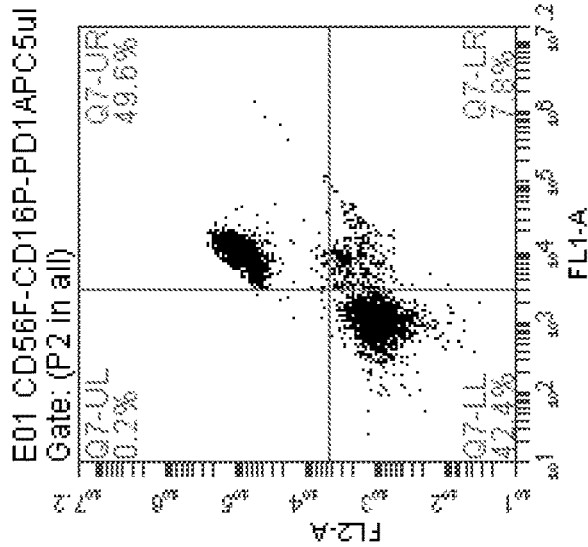

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The terms "treatment" and "treating" as used herein may refer to a curative or palliative measure. In particular, the term "treating" as used herein refers to the application or administration of the present mTOR inhibitor and chloroquine or analogue thereof or a pharmaceutical composition or kit comprising the same to a subject, who has prostate cancer, a symptom associated with prostate cancer, a disease or disorder secondary to prostate cancer, with the purpose to partially or completely alleviate, ameliorate, relieve, delay onset of, inhibit progression of, reduce severity of, and/or reduce incidence of one or more symptoms or features of prostate cancer.

The terms "subject" and "patient" are used interchangeably herein and are intended to mean an animal including the human species that is treatable by the mTOR inhibitor and chloroquine or analogue thereof, pharmaceutical composition or kit, and/or method of the present invention. The term "subject" or "patient" intended to refer to both the male and female gender unless one gender is specifically indicated.

The terms "application" and "administration" are used interchangeably herein to mean the application of the mTOR inhibitor and chloroquine or analogue thereof or a pharmaceutical composition or kit of the present invention to a subject in need of a treatment thereof.

The term "effective amount" as used herein refers to the quantity of the present mTOR inhibitor and chloroquine or analogue thereof that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, as the total mass of ester prodrug (e.g., in grams, milligrams or micrograms) or a ratio of mass of ester prodrug to body mass, e.g., as milligrams per kilogram (mg/kg).

The phrase "pharmaceutically acceptable excipient" as used herein means a pharmaceutically acceptable material, composition or vehicle, such as a liquid or solid filler, diluent, carrier, solvent or encapsulating material, involved in carrying or transporting the subject agents from one organ, or portion of the body, to another organ, or portion of the body. Each excipient must be "acceptable" in the sense of being compatible with the other ingredients of the formulation. The pharmaceutical formulation contains a compound of the invention in combination with one or more pharmaceutically acceptable ingredients. The excipient can be in the form of a solid, semi-solid or liquid diluent, cream or a capsule. These pharmaceutical preparations are a further object of the invention. Usually, the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, the pharmaceutical composition of the invention is formulated into formulations suitable for the intended route of administration.

[define "unresponsive or not response well to hormone therapy and/or immunotherapy", by referring to the NK cell activity and NK cell subpopulation]

The present disclosure is based, at least in part, on the discovery that to a patient who is not responsive or does not response well to a hormone therapy and/or immunotherapy, the administration of an mTOR inhibitor and chloroquine or analogue thereof sensitizes the patient's response to said hormone therapy and immunotherapy. In view of the foregoing, the present disclosure provides methods for treating cancer patients; in particular, those who do not response well to previous hormone therapy and/or immunotherapy. Also provided herein is the use of said mTOR inhibitor and chloroquine or analogue thereof in the treatment of said cancer patients, as well as in the manufacture of a medicament for said treatment purpose. The medicament (i.e., a pharmaceutical composition or kit) is, of course, a subject matter covered by the scope of the present application.

In one aspect, the present disclosure is directed to a method for treating a cancer patient who is unresponsive to a hormone therapy and/or an immunotherapy.

According to various embodiments of the present disclosure, the method comprises the step of administering to said cancer patient an effective amount of an mTOR inhibitor and an effective amount of chloroquine or an analogue thereof, during the treatment of the hormone therapy and the immunotherapy.

According to various embodiments of the present disclosure, the mTOR inhibitor may be the first generation or second generation mTOR inhibitors. Most first generation mTOR inhibitors are rapamycin and rapamycin analogues (also known as rapalogs), such as sirolimus, temsirolimus, everolimus, and deforolimus. The second generation of mTOR inhibitors is known as ATP-competitive mTOR kinase inhibitors, which are mTORC1/mTORC2 dual inhibitors designed to compete with ATP in the catalytic site of mTOR. In contrast to rapalogs that only target mTORC1, these ATP-competitive mTOR kinase inhibitors inhibit the kinase-dependent functions of both mTORC1 and mTORC2.

In optional embodiments, the chloroquine analogue is hydroxychloroquine.

As could be appreciated, the mTOR inhibitor and chloroquine or analogue thereof can be formulated into one pharmaceutical composition. Alternatively, the mTOR inhibitor and chloroquine or analogue thereof may be formulated individually, and then presented as a pharmaceutical kit. Either way, the mTOR inhibitor and/or chloroquine or analogue thereof can be formulated, together with a pharmaceutically-acceptable excipient, into a pharmaceutical composition suitable for the desired mode of administration. Certain pharmaceutical compositions prepared in accordance with the presently disclosed and claimed inventive concept(s) are single unit dosage forms suitable for oral administration to a patient. Examples of oral dosage forms include, but are not limited to, tablets, caplets; capsules (e.g., elastic gelatin capsules), cachets, troches, powders, suspensions (e.g., aqueous or non-aqueous liquid suspensions, oil-in-water emulsions, or a water-in-oil liquid emulsions), dispersions, solutions, and elixirs. As could be appreciated, these pharmaceutical compositions or kits are also within the scope of the present disclosure.

It should be noted that during the term of the present treatment, different therapies or therapeutics may be administered to the cancer patients at different time intervals via different routes. For example, certain therapeutics for the hormone therapy may be given monthly (e.g., leuprolide (LEUPLIN®) for subcutaneous or intramuscular injection), while some hormone therapy therapeutics are given twice per day (e.g., cyproterone acetate (ANDROCUR®) for oral administration or intramuscular injection). As to therapeutics commonly used in immunotherapies (such as antibodies, interferons, and interleukins), these drugs are often given at intervals of one, two, three, or four weeks. For instance, the anti-PD1 antibody, pembrolizumab (KEYTRUDA®) is given every three weeks, i.v., while nivolumab (OPDIVO®) is often administered every two weeks. On the other hand, the mTOR inhibitor, as well as the chloroquine or analogue thereof, is often formulated in the tablet form, and given in one or more doses daily.

In various embodiments, the subject is a mammal, which may benefit from the treatment method of the present disclosure. As used herein, "mammal" refers to all members of the class Mammalia, including humans; primates (e.g., monkey and chimpanzee); domestic and farm animals, such as dog, cat, rabbit, pig, sheep, goat, cow, horse, and cattle; as well as zoo, sports or pet animals; and rodents, such as mouse, rat and guinea pig. In an exemplary embodiment, the patient is a human.

According to various embodiments of the present disclosure, the cancer patient is diagnosed with melanoma, esophageal carcinoma, gastric carcinoma, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, or head and neck squamous cell carcinoma. According to certain embodiments, the cancer patient is diagnosed with prostate cancer; in particularly, metastatic prostate cancer.

Yet another aspect of the present disclosure is direct to the use of an mTOR inhibitor and chloroquine or analogue thereof in the manufacture of a medicament, which may be use in the treatment of a cancer patient who is not responsive or does not responsive well to a previous hormone therapy and/or immunotherapy, and the medicament is administered during a combined treatment of the hormone therapy and immunotherapy. Still another aspect of the present disclosure is direct to the use of an mTOR inhibitor and chloroquine or analogue thereof in the treatment of cancer patient during a combined treatment of a hormone therapy and an immunotherapy, wherein the cancer patient is not responsive or does not responsive well to a previous hormone therapy and/or immunotherapy. As could be appreciated, the various mTOR inhibitors and chloroquine or analogues thereof described above are also applicable in these aspects.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

Example 1

A 69 year old male patient with prostate cancer and bony metastasis had been treated by hormone therapy (Leuplin, 3.6 mg s.c. per month and oral Androcur 1 tablet bid) for one year with initial response but then the tumor progressed slowly. After recurrence, the patient received the same hormone therapy plus anti-PD1 therapy (Pembrolizumab, 150 mg every 3 weeks) for 3 cycles; however, the patient showed no sign of response and an elevated serum prostate-specific antigen (PSA) level was detected as tumor progressively developed.

Since the patient was not responsive to the combination of the hormone therapy and immunotherapy, the patient was then given the same hormone therapy plus daily administration of chloroquine (400 mg) and rapamycin (2 mg) for another three months. Yet, the patient did not respond to this combined treatment either.

Figure 2:
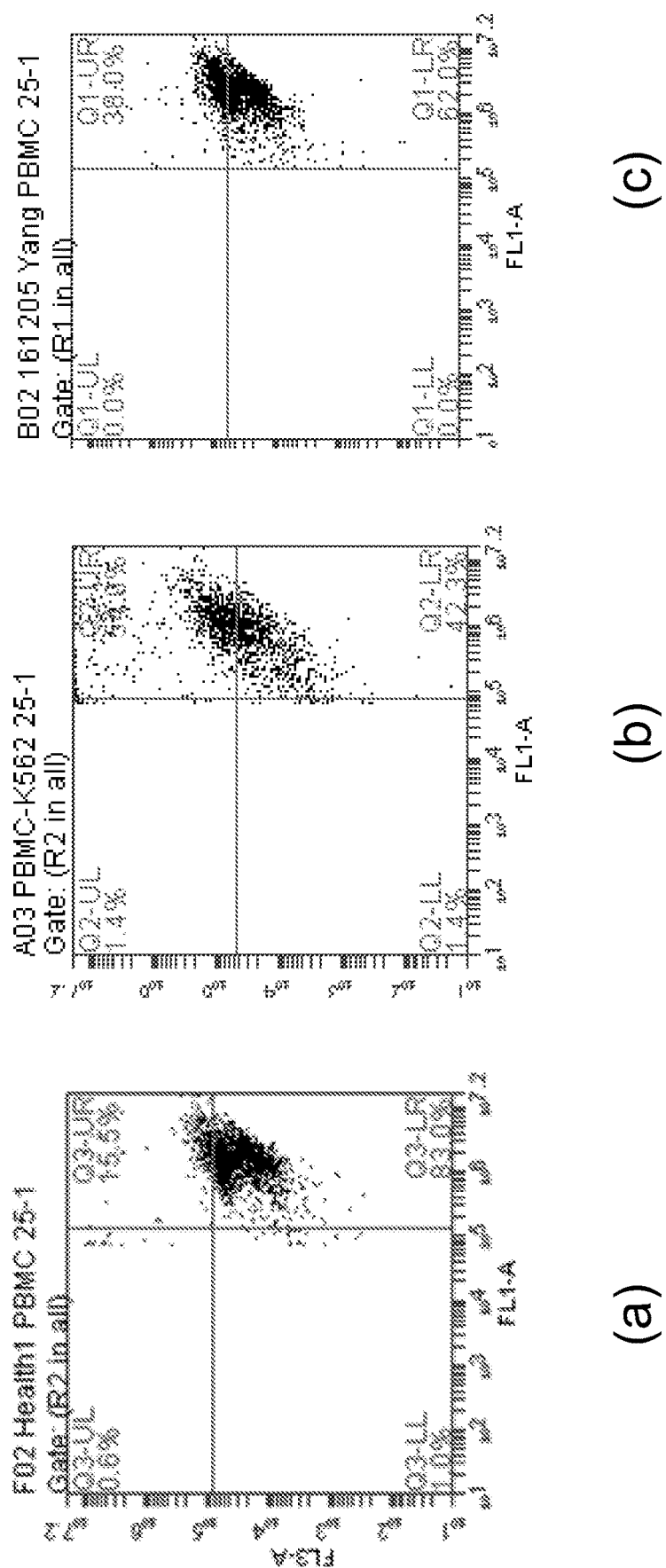

After this treatment and before the commencement of the present treatment, the percentages of monocyte and lymphocyte, as well as the percentages of CD3+, CD4+ and CD8+T cell subpopulations, B cells, regulatory T cells (Treg), and NK cells in the peripheral blood mononuclear cells (PBMCs) of the patient were determined. PBMCs were also co-cultured with K562 cells (PBMC:K562=25:1) for 16 hours to investigate the cytotoxic activity of NK cells from PBMCs against K562 target cells. Briefly, the cells were cultured using 10% FBS RPMI. The data as summarized in column A of Table 1 below and panel (a) of FIG. 1, indicated the T cell subpopulations accounted for a smaller proportion of PBMCs while the natural killer (NK) cell represented approximately half of the PBMCs. However, the activity of NK cells remained low (about 15% cytotoxicity) despite the elevated NK cell subpopulation (about 49.6%) in PBMCs (see, column A, Table 1, and panel (a), FIG. 2).

TABLE 1

|  | A | B | C |
|---|---|---|---|
| Monocyte (%) | 15 | 13.7 | 11 |
| Lymphocyte (%) | 78 | 80 | 86.5 |
| Lymphocyte (%) | | | |
| CD3+ | 34.6 | 39.6 | 40.4 |
| CD4+ | 22.3 | 21 | 21.8 |
| CD8+ | 29.9 | 33.8 | 30.7 |
| B cells | 10.5 | 8.2 | 5.7 |
| Treg | 0.9 | 0.8 | 1.1 |
| NK | 49.6 | 37.7 | 47.8 |
| 16 hr NK cytotoxicity (%) | | | |
| PBMC:K562 = 25:1 | 15 | 50.1 | 33.5 |

In view of such finding, the patient was then given the combined treatment of the same hormone therapy plus anti-PD1 therapy plus daily administration of chloroquine (400 mg) and rapamycin (2 mg) for additional two months. Referring to column B, Table 1, one week after the present combined treatment, a decrease in NK cell subpopulation (about 37.7%) in PBMCs was observed, while a significant increase in NK cell cytotoxicity (about 50.1%) was exhibited. After three weeks of the combined treatment, see column C of Table 1, and panel (c) of FIGS. 1 and 2, the NK cell subpopulation increased to about 47.8%, which was quite close to the level before the present combined treatment started, but the NK cell cytotoxicity was about 33.5%, which was more than twice of the NK cell cytotoxicity before the treatment.

In addition to the marked increase in the NK cell cytotoxicity after the present combined treatment, the PSA level in the patient also decreased, and several clinical symptoms clearly improved.

Taken together, the present combined treatment, which comprised the use of mTOR inhibitor, chloroquine or analogue thereof, is an effective treatment for cancer patient that does not respond to hormone therapy and immunotherapy.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating a cancer patient who is unresponsive to a hormone therapy and an immunotherapy consisting of administering to the patient (a) an effective amount of leuprolide and pharmaceutically acceptable excipient, (b) an effective amount of an anti-PD-1 antibody and pharmaceutically acceptable excipient, (c) an effective amount of sirolmus and pharmaceutically acceptable excipient, and (d) an effective amount of chloroquine or hydroxychloroquine and pharmaceutically acceptable excipient; wherein the cancer patient is diagnosed with a breast cancer, an ovary cancer, a prostate cancer, or a thyroid cancer.

2. The method of claim 1, wherein the anti-PD-1 antibody is nivolumab, pembrolizumab, or pidilizumab.

3. The method of claim 1, wherein the cancer patient is diagnosed with a prostate carcinoma.

4. The method of claim 1, wherein sirolmus and chloroquine or hydroxychloroquine improves the cytotoxic activity of natural killer cells of the cancer patient.

5. A method for treating a cancer patient who is unresponsive to a hormone therapy and an immunotherapy consisting of administering to the patient (a) an effective amount of leuprolide and pharmaceutically acceptable excipient, (b) an effective amount of cyproterone acetate and pharmaceutically acceptable excipient, (c) an effective amount of an anti-PD-1 antibody and pharmaceutically acceptable excipient, (d) an effective amount of sirolmus and pharmaceutically acceptable excipient, and (e) an effective amount of chloroquine or hydroxychloroquine and pharmaceutically acceptable excipient; wherein the cancer patient is diagnosed with a breast cancer, an ovary cancer, a prostate cancer, or a thyroid cancer.

6. The method of claim 5, wherein the anti-PD-1 antibody is nivolumab, pembrolizumab, or pidilizumab.

7. The method of claim 5, wherein the cancer patient is diagnosed with a prostate carcinoma.

8. The method of claim 5, wherein sirolmus and chloroquine or hydroxychloroquine improves the cytotoxic activity of natural killer cells of the cancer patient.

* * * * *